United States Patent
Windridge et al.

(10) Patent No.: US 10,049,645 B2
(45) Date of Patent: Aug. 14, 2018

(54) CONTROL DEVICE AND METHOD FOR OPTIMIZING A PRESENTATION STYLE OF SPECIFIC CONTENT FOR A SPECIFIC USER

(71) Applicant: KONINKLIJKE PHILIPS N.V., Eindhoven (NL)

(72) Inventors: Melanie Jane Windridge, Amersham (GB); Julian Charles Nolan, Pully (CH); Joyca Petra Wilma Lacroix, Eindhoven (NL); Joris Hendrik Janssen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/105,040

(22) PCT Filed: Dec. 12, 2014

(86) PCT No.: PCT/EP2014/077476
§ 371 (c)(1),
(2) Date: Jun. 16, 2016

(87) PCT Pub. No.: WO2015/091228
PCT Pub. Date: Jun. 25, 2015

(65) Prior Publication Data
US 2016/0322028 A1 Nov. 3, 2016

(30) Foreign Application Priority Data
Dec. 20, 2013 (EP) .................................. 13198796

(51) Int. Cl.
*G06F 3/01* (2006.01)
*G06F 3/048* (2013.01)
(Continued)

(52) U.S. Cl.
CPC ............... *G09G 5/30* (2013.01); *A61B 5/044* (2013.01); *A61B 5/4833* (2013.01); *A61B 5/742* (2013.01);
(Continued)

(58) Field of Classification Search
CPC ..... G09G 5/30; G06F 17/214; G06F 19/3406; G06F 3/011; A61B 5/4833; A61B 5/742
(Continued)

(56) References Cited

U.S. PATENT DOCUMENTS 6,206,702 B1   3/2001  Hayden et al.
7,186,116 B2   3/2007  Klinkberg
(Continued)

FOREIGN PATENT DOCUMENTS

CN   103220386 A    7/2013
WO   2013026725 A1  2/2013

OTHER PUBLICATIONS

Diemand-Yaumand, "Fortune Favaors the Bold and Thei Talicized: Effects of Disfluency on Educational Outcomes", Cognition, 2010, pp. 1-5.
(Continued)

*Primary Examiner* — Jin-Cheng Wang

(57) ABSTRACT

The present invention relates to a control device (10) and method for controlling a display that reliably and efficiently enhances a person's compliance, e.g., a patient's compliance with his care plan. The control device comprises a presentation style selector (14) for selecting a presentation style to be used for visually presenting the received information on the display in text form, wherein the presentation style is selected based on an importance indicator indicating the importance of the information with respect to a task or plan of the person and obtained boundary conditions for the presentation style to be selected for presenting the informa-
(Continued)

| 1  | EASY   | ○ Verdana (black on white) |
| 2  |        | ○ Verdana (grey on black)  |
| 3  |        |                            |
| 4  |        |                            |
| 5  | MEDIUM | ○ Times New Roman          |
| 6  |        | ○ Times New Roman          |
| 7  |        |                            |
| 8  |        |                            |
| 9  | HARD   | ○ *Edwardian Script*       |
| 10 |        | ○ *Edwardian Script*       | tion in text form such that more important information is displayed using a presentation style that is more difficult to read than a presentation style used for displaying less important information. A controller (15) controls the display (20) to visually present the received information on the display in text form using the selected presentation style.

13 Claims, 5 Drawing Sheets

(51) Int. Cl.
*G06F 17/21* (2006.01)
*A61B 5/00* (2006.01)
*G09G 5/30* (2006.01)
*G06F 19/00* (2018.01)
*G06F 8/34* (2018.01)
*A61B 5/044* (2006.01)
*G16H 40/63* (2018.01)

(52) U.S. Cl.
CPC ............ *A61B 5/743* (2013.01); *G06F 3/011* (2013.01); *G06F 8/34* (2013.01); *G06F 17/214* (2013.01); *G16H 40/63* (2018.01); *A61B 5/7435* (2013.01); *A61B 5/7445* (2013.01)

(58) Field of Classification Search
USPC .................................. 705/2, 3; 715/744, 800
See application file for complete search history.

(56) References Cited

U.S. PATENT DOCUMENTS

| | | | |
|---|---|---|---|
| 7,326,058 B2 | 2/2008 | Abraham-Fuchs et al. | |
| 8,273,020 B2 | 9/2012 | Robinson et al. | |
| 2005/0060186 A1* | 3/2005 | Blowers | G06Q 50/22 705/2 |
| 2007/0156382 A1 | 7/2007 | Graham, II et al. | |
| 2010/0324937 A1* | 12/2010 | Sriyapareddy | G06Q 50/24 705/3 |
| 2011/0179361 A1* | 7/2011 | Cardarelli | A61B 5/0002 715/744 |
| 2013/0179472 A1 | 7/2013 | Junqua et al. | |
| 2013/0198685 A1* | 8/2013 | Bernini | G06F 3/0484 715/800 |

OTHER PUBLICATIONS

Bernard et al, "A Comparison of Popular Online Fonts: Which Size and Type is Best?", Software Usability Research Laboratory, Downloaded From http://usabilitynews.org/a-comparison-of-popular-online-fonts-which-size-and-type-is-Best/ on Jun. 14, 2016, 8 Pages.
Arditi et al, "Serifs and Font Legibility", Vision Research, vol. 45, Issue 23, 2005, pp. 2926-2933.
Rayner et al, The Effect of Word Frequency, Word Predictability, and Font Difficulty on the Eye Movements of Young and Older Readers, Psychology and Aging, vol. 21, No. 3, 2006, pp. 448-465.
Levels-of-Processing Effect, Downloaded From http://en.wikipedia.org/wiki/levels-of-processing_effect on Jun. 13, 2016, 7 Pages.
Munoz et al, "Designing Context-Aware Interactions for Task-Based Applications", In: Daniel F. and Facca F.M.: Current Trens in Web Engineering, 2010, pp. 463-473.
Stone, "A New Program Automatically Adjusts Your Font to a Readablesize", Retrieved From http://fastcoexist.com/1681393/a-new-program-automatically-adjusts-your-font-to-a-readable-size#comment-62c1a000-7703-11e2-9be6-2D6de8fb2111,on May 2, 2014.
E-Readers 'Too Easy' to Read, Downloaded From http:///www.telegraph.co.uk/technology/amazon/8256899/e-readers-too-easy-to-read.html on Jun. 14, 2016, 2 Pages.
Adee, "Ricksy Type: How Fonts Can Mess With Your Mind", Downloaded From http://www.newscientist.com/article/mg21628962.600-tricksy-type-how-fonts-can-mess-with-your-mind.html on Jun. 14, 2016, 3 Pages.
Open Dyslexic, Downloaded From http://opendyslexic.org/ on Jun. 14, 2016, 2 Pages.

* cited by examiner

| 1 | EASY | ○ Verdana (black on white) |
| 2 | | ○ Verdana (grey on black) |
| 3 | | |
| 4 | | |
| 5 | MEDIUM | ○ Times New Roman |
| 6 | | ○ Times New Roman |
| 7 | | |
| 8 | | |
| 9 | HARD | ○ *Edwardian Script* |
| 10 | | ○ *Edwardian Script* |

CONTROL DEVICE AND METHOD FOR OPTIMIZING A PRESENTATION STYLE OF SPECIFIC CONTENT FOR A SPECIFIC USER

CROSS-REFERENCE TO PRIOR APPLICATIONS

This application is the U.S. National Phase application under 35 U.S.C. § 371 of International Application No. PCT/EP2014/077476, filed on Dec. 12, 2014, which claims the benefit of European Patent Application No. 13198796.8, filed on Dec. 20, 2013. These applications are hereby incorporated by reference herein.

FIELD OF THE INVENTION

The present invention relates to a control device and a corresponding control method for controlling a display. The present invention relates further to a system for increasing the compliance of a person with a task or plan and to a computer program for implementing said control method.

BACKGROUND OF THE INVENTION

The level of cognitive engagement with presented information affects the way a person perceives and retains information. Cognitive engagement can be increased by increasing the effort required to read and understand the presented information, for example by using a harder-to-read font. With harder-to-read fonts more details are retained but tasks are perceived to be harder, longer or more arduous. There may also be medical reasons, such as dyslexia, which affect people's ability to read. Some fonts have been designed to aid the reading process for dyslexics.

It is common to alter the appearance of fonts for different people, for example increasing font size for the vision-impaired. An example of this is the service "iReminder.com Compliance for Life" that provides treatment reminders including customizable text according to wishes of the patient. Further, advances in technology such as gaze recognition may be used to provide a measure of reading speed, which may be linked to cognitive engagement.

Many patients do not comply fully with their care plan. This could be due to a number of reasons, which may include forgetting important information or perceiving required tasks as too arduous or inconvenient. Non-adherence to a medication regimen and/or other aspects of a care plan is accountable for a high percentage of healthcare readmission's costs. In order to increase adherence and compliance, several proposals have been made, from psychological profiling to automatic pill dispensers.

Non-compliance can be a result of a lack of knowledge how to comply correctly to a doctor's recommendations, due to an insufficient processing of information presented to a patient. A lack of sufficiently deep processing may result in an ability to appropriately encode the information in memory and recall it at a later moment. Lack of sufficient processing may result for example from a lack of attention of the patient, because the information is not perceived as interesting or a lack of effort from the patient's side because the task is perceived as too difficult. There is a need to present information to a person in such a way that deep processing of the information is stimulated, i.e. to improve the cognitive effort for processing the information which leads to a beneficial effect on the memory.

Munoz P, Giner P. and Gil M.: "Designing Context-Aware Interactions for Task-Based Applications" in: Daniel F. and Facca F. M.: "Current Trends in Web Engineering, ICWE 2010 Workshops", July 2010, Springer, Heidelberg, pages 463-473, discloses an approach for integrating contextual information in task-based applications by considering simplicity as a major design goal is presented. In particular, a context-aware application is presented to support mobile workflows focusing the described solutions in three important factors to organize and manage tasks: priority, location and time. Following the simplicity guidelines, solutions are provided based on these factors by means of visualizations that allow users to complete their tasks fluently on the go.

SUMMARY OF THE INVENTION

It is an object of the present invention to provide a control device and a corresponding control method for controlling a display that reliably and efficiently enhances a person's depth of processing of presented information and consequently increases the likelihood of a person to comply with the presented information, e.g. a patient's compliance with his care plan. The present invention relates further to a system for increasing the compliance of a person with a task or plan and to a computer program for implementing said control method.

In a first aspect of the present invention a control device is presented comprising an input interface for receiving information to be visually presented to a person on a display in text form, an importance indicator unit for obtaining an importance indicator indicating the importance of the information with respect to a task or plan of the person, a data analyzer for analyzing personal data relating to the person to be presented with the information to obtain personalized boundary conditions for the presentation style to be selected for presenting the information in text form to the person, said personalized boundary conditions indicating potential presentation styles that may be used for presenting information to the person, and a presentation style selector for selecting a presentation style to be used for visually presenting the received information on the display in text form, wherein the presentation style is selected based on the importance indicator and the obtained boundary conditions such that more important information is displayed using a presentation style that is more difficult to read than a presentation style used for displaying less important information, and a controller for controlling the display to visually present the received information on the display in text form using the selected presentation style.

In a further aspect of the present invention a system for increasing the compliance of a person with a task or plan is presented comprising a control device disclosed herein, and a display for visually presenting received information in text form using a selected presentation style as selected by the control device.

In yet further aspects of the present invention, there are provided a control method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed system and as defined in the dependent claims.

It has been found that the fluidity of the presentation style in which information is displayed has an effect on the perception of task difficulty and on information retention, due to the way the brain processes the different presentation styles (i.e., the amount of effort and elaboration required to process the information). Hence, the present invention is based on the idea to enable adjusting the presentation styles used to display information based on the desired depth of processing used by the brain to process this information in order to improve the person's compliance with a plan or task. The presentation of information to a person, e.g. a patient, is thus varied based on the content and context of the message taken into account by an importance indicator indicating the importance of the information with respect to a (preferably predetermined) task or plan of the person. In this context importance of information shall be understood as the expected level of impact that the information has on outcomes (e.g., when considering health outcomes of a patient, instructions that medicaments should be taken every day prior to dinner has a higher importance than information about the availability of an alternative generic medication; and e.g., in case of education outcomes (performance at school), the importance of educative content varies). Preferably, for instance, less important information is presented in an easier-to-read presentation style and more important information is presented in a harder-to-read presentation style. Easier-to-read and harder-to-read may hereby be defined differently for each person or each group/type of person, as indicated for example by the person's vision and attention span. More difficult to read may e.g. be understood as requiring more efforts by the reader to read the text. Examples for fonts that are considered as fonts that are harder to read include, but are not limited to Comic Sans, Bodoni MT, Haettenschweiler, Monotype Corsiva, e.g. 12-point Comic Sans MS, Comic Sans Italicized or Bodoni MT in a lighter shade. Examples for fonts that are considered as fonts that are easier to read include, but are not limited to Georgia, Times New Roman, Verdana, and Arial, e.g. 16-point Arial pure black. Further explanations will be given below.

If a person invests more cognitive effort, processing of the presented information is more in-depth and memory retention is improved and as a consequence the likelihood of complying with the information increases because the information remains available to the person in memory. This works by just using variations in presentation style.

Further, there is also an effect on perceived effort of the content of the presented information or message (both terms being used herein interchangeably and equivalently). This explains why not just everything should be presented in a presentation style that requires a lot of effort. As such, choosing the presentation style requires a delicate consideration of the tradeoff between memory benefits at the cost of increased perceived effort of execution (which may hamper compliance). Hence, by use of the present invention the optimum presentation style may be found for a specific message/information for a specific person.

Various options for selection the presentation style are generally available. Such options include, but are not limited to font, font style, font size, font color, underline style, text effects (e.g. shadow, 3D effect, strikethrough, outline, etc.) and/or character spacing. In an embodiment the font presentation style selector is accordingly configured to select one or more these options of the presentation style, text style relating to vocabulary and sentence structure (e.g., more complicated sentence structure and/or more difficult synonyms).

Further, according to the present invention personalized boundary conditions for the presentation style are defined. For instance, as proposed in an embodiment said data analyzer is configured to obtain said boundary conditions by analyzing the person's profile including information on age, eyesight and/or ophthalmic problems of the person. Thus, the person is assigned a pre-defined "presentation style band" from which the presentation style for presentation will be selected.

This may, for instance, be done by performing a test with the person and/or by analyzing gaze and/or scrolling of the person of the person during reading text displayed on the display. For instance, a game-style test may be used to determine the presentation style band and person-specific optimal presentation styles for retention and motivation. As an example, a person may be presented with different characters and information in various presentation style, e.g. various font sizes and fonts, and tested on what he has seen, retained and perceived.

In another embodiment said input interface is configured to receive a predetermined plan to be complied with by the person, said plan including information to be presented to the person, and to extract the information to be presented to the person from the received plan. Such text mining is generally known in the art, as currently e.g. disclosed at http://en.wikipedia.org/wiki/Text_mining. It may be implemented using well known search and semantic computing techniques.

Preferably, said importance indicator unit is configured to receive said importance indicator as input and/or to analyze the content and/or context of the received information to get the importance indicator. The importance indicator may e.g. be tagged by a care giver who defines a care plan. For instance, certain important information may be tagged with a binary IMPORTANT/NOT IMPORTANT status or a scale of discrete integers (e.g. 1 through 5 etc.) Alternatively, importance may be scored by posting the care plan on a website or forum, and receiving votes from the person's friends and family or peers. Still further, the importance indicator may also be determined by using a template for the person's condition, which highlights important aspects of the care plan, and is overlaid onto the person's actual care plan. Also, the content of the information may be analyzed automatically on containing specific essential key words that are indicative of importance (e.g., when the information contains words related to medication intake, this indicates a high importance for a patient). Or if there are, for example, specific key words that illustrate the necessity of an action such as 'must' or 'have to' can be said to be of higher importance than words that illustrate the possibility of an action such as 'may', or 'can'.

In another embodiment said input interface is configured to receive person-related location data and/or movement data indicating the location and/or the movement state of the person, wherein said controller is configured to select the presentation style based on the importance indicator and the received person-related location data and/or movement data. It has been found that also the location and/or movement of a person has an influence on the person's perception. For instance, when a person is moving a presentation style that is easier to read should be used compared to when the person is stationary.

Preferably, said input interface is configured to receive person-related schedule data indicating the person's schedule, wherein said controller is configured to control the display to visually present the received information at a time convenient to the person according to the person's schedule. This will generally also increase the person's perception.

In a further improvement said input interface is configured to receive compliance data and/or sympathetic autonomic activity data indicating the person's compliance and/or sympathetic autonomic activity with a task or plan while or after being presented with information using a selected presentation style, wherein said controller is configured to adapt and/or select the presentation style for the current and/or later presentation of information based on the importance indicator and on the received compliance data and/or sympathetic autonomic activity data. In this way a kind of learning system can be established to find the optimum presentation style for a particular person to obtain the optimum compliance and/or sympathetic autonomic activity.

It is further preferred that said importance indicator unit is configured to categorize the received information based on the type of the information, the importance of the information and the number of previous presentations of the information, wherein said controller is configured to select the presentation style based on the importance indicator and obtained categories of the received information. This further helps in finding the optimum presentation style for a particular person.

Still further, in an embodiment said input interface is configured to receive the person's health literacy level, psychological profile, preference for presentation style (e.g., visual or text) and/or education level, wherein said controller is configured to select the presentation style of the information based on the importance indicator and on the received health literacy level, psychological profile, preference for presentation style and/or education level It should be noted that presentation style is one way to enhance the cognitive effort required for processing and achieving the beneficial effect on memory or an effect on perceived effort. More ways to trigger a more or less in-depth cognitive processing used in addition according to preferred embodiments, such as using terms that have a personalized "intellectual challenge level" depending on someone's health literacy level. For instance, keeping a database of synonyms of terms that vary in the effort required to process them but refer to the same thing is proposed in an embodiment.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
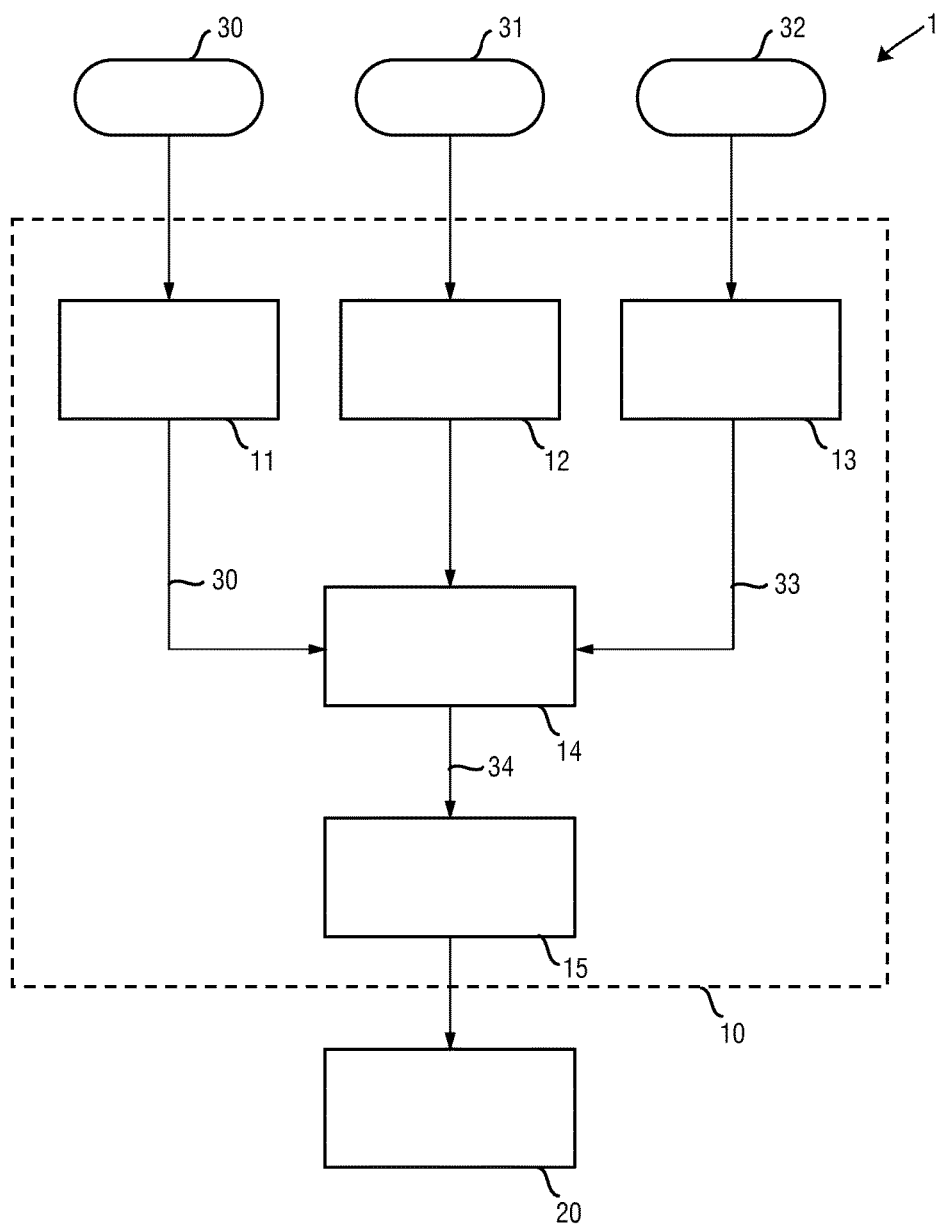
FIG. 1 shows a schematic diagram of an embodiment of a control device and a system according to the present invention.

FIG. 1 shows a schematic diagram of an embodiment a system 1 for increasing the compliance of a person with a (preferably predetermined) task or plan according to the present invention. Said system 1 includes an embodiment of a control device 10 according to the present invention and a display 20, wherein said control device 10 is configured to control the display to visually present the information related to the task or plan on the display 20 in text form.

The control device 10 particularly comprises an input interface 11 for receiving information 30 to be visually presented to a person on the display 20 in text form. An importance indicator unit 12 is provided for obtaining an importance indicator 31 indicating the importance of the information with respect to a task or plan of the person. A data analyzer 13 is provided for analyzing personal data 32 relating to the person to be presented with the information in order to obtain boundary conditions 33 for the presentation style to be selected for presenting the information in text form. In particular, a presentation style indicator is obtained indicating potential presentation styles that may be used. A presentation style selector 14 is provided for selecting a presentation style 34 to be used for visually presenting the received information on the display in text form, wherein the presentation style is selected based on the importance indicator and the obtained boundary conditions (of the person) such that more important information is displayed using a presentation style that is more difficult to read than a presentation style used for displaying less important information. Finally, a controller 15 is provided for controlling the display 20 to visually present the received information on the display in text form using the selected presentation style.

The various units of the control device may be comprised in one or multiple digital or analog processors depending on how and where the invention is applied. The different units may completely or partly be implemented in software and carried out on a personal computer or processor. Some or all of the required functionality may also be implemented in hardware, e.g. in an application specific integrated circuit (ASIC) or in a field programmable gate array (FPGA).

With respect to the question which presentation style are easier to read that other presentation styles, which require more efforts for reading by the reader, various studies have been made. The findings of these studies may be exploited by the present invention, and the content and findings of these studies is herein incorporated by reference.

In the publication "Fortune favors the Bold and the Italics: Effects of disfluency on educational outcomes" by Connor Diemand-Yauman, Daniel M. Oppenheimer, Erikka B. Vaughan, 2010 Elsevier B. V., currently published at http://web.princeton.edu/sites/opplab/papers/Diemand-Yauman_Oppenheimer_2010.pdf two studies explore the extent to which this deeper processing engendered by disfluency interventions can lead to improved memory performance. Study 1 found that information in hard-to-read fonts was better remembered than easier to read information in a controlled laboratory setting. Study 2 extended this finding to high school classrooms. The results suggest that superficial changes to learning materials could yield significant improvements in educational outcomes.

In the publication "A Comparison of Popular Online Fonts: Which Size and Type is Best?" by Michael Bernard, Bonnie Lida, Shannon Riley, Telia Hackler, & Karen Janzen, currently published at http://usabilitynews.org/a-comparison-of-popular-online-fonts-which-size-and-type-is-best/ several observations are made regarding the examined font types. First, no significant differences in reading efficiency were detected between the font types at any size. There were, however, significant differences in reading time. Generally, Times and Arial were read faster than Courier, Schoolbook, and Georgia. Fonts at the 12-point size were read faster than fonts at the 10-point size. In addition, a font type×size interaction was found for the perception of font legibility. In general, however, Arial, Courier, and Georgia were perceived as the most legible.

For font attractiveness, Georgia was perceived as being more attractive than Arial, Courier, and Comic, while Times was perceived as more attractive than Courier. This contrasts with participants' general preference for a particular font type. Overall, Verdana was the most preferred font, while Times was the least preferred. Thus it seems that the Georgia and Times serif fonts are considered more attractive, but they are generally less preferred. Of the fonts studied, Verdana appears to be the best overall font choice. Besides being the most preferred, it was read fairly quickly and was perceived as being legible.

In the publication "Serifs and font legibility" by Aries Arditi, Jianna Cho, Volume 45, Issue 23, November 2005, pages 2926-2933, using lower-case fonts varying only in serif size (0%, 5%, and 10% cap height) was assessed regarding legibility using size thresholds and reading speed. Five percentage serif fonts were slightly more legible than sans serif, but the average inter-letter spacing increase that serifs themselves impose, predicts greater enhancement than observed. Rapid serial visual presentation and continuous reading speeds showed no effect of serifs. When text is small or distant, serifs may, then, produce a tiny legibility increase due to the concomitant increase in spacing. However, the data exhibited no difference in legibility between typefaces that differ only in the presence or absence of serifs.

In the publication "The Effect of Word Frequency, Word Predictability, and Font Difficulty on the Eye Movements of Young and Older Readers", by Keith Rayner et al., Psychology and Aging 2006, Vol. 21, No. 3, 448-465 Young adult and older readers' eye movements were recorded as they read sentences containing target words that varied in frequency or predictability. In addition, half of the sentences were printed in a font that was easy to read (Times New Roman) and the other half were printed in a font that was more difficult to read (Old English). Word frequency, word predictability, and font difficulty effects were apparent in the eye movement data of both groups of readers. In the fixation time data, the pattern of results was the same, but the older readers had larger frequency and predictability effects than the younger readers. The older readers skipped words more often than the younger readers (as indicated by their skipping rate on selected target words), but they made more regressions back to the target words and more regressions overall. The E-Z Reader model was used as a platform to evaluate the results, and simulations using the model suggest that lexical processing is slowed in older readers and that, possibly as a result of this, they adopt a more risky reading strategy. When one reads, one does not see individual letters. One sees (and reads) the shapes of the words. These shapes are primarily created by two elements: the strokes of the letters, and the spaces in and around the letters. If either of these elements is lost, legibility is compromised.

For instance, multiple-generation photocopies make the text lighter Thinner strokes start to disappear, leaving only parts of letters and compromising the word shapes. Other times, multiple-generation photocopies make the strokes in the text thicker. The spaces in and around the letters start to disappear. Either way, when strokes or spaces get lost, the legibility of the font changes and reading becomes more difficult.

Web typographers need to pay particular attention to the strokes and spaces in a font because of screen resolution. Macintosh screens are 72 ppi (pixels per inch), and Windows screens are 96 ppi. A font set at 12 px will appear approximately ⅛" tall on a Mac and less than ⅛" tall on a Windows screen. In either case, the screen will have (at most) 12 px by 12 px to render a letter. Thin strokes and small spaces in letterforms will start to disappear. And, as in the photocopy example, the text will be harder to read. Thus, "simple" fonts are generally better for the screen because of the resolution issues.

Figure 2:
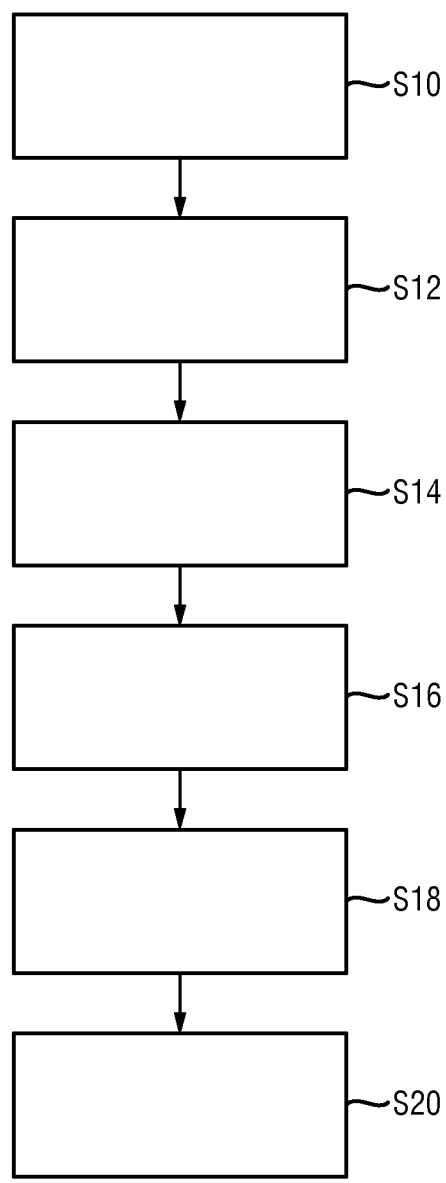
FIG. 2 shows a flow chart of an embodiment of a control method according to the present invention.

In the following a more detailed embodiment of the proposed control method is described with reference to FIG. 2. Said control method may be carried out by the controller 10 and the system 1 shown in FIG. 1. It shall be noted that this embodiment of the control method refers to the non-limiting example of a patient whose compliance with a care plan shall be enhanced and to the selection of the optimal font (as one particular example of the presentation style) The present invention is, however, neither limited to this exemplary embodiment nor to such an application of the invention.

In a first step S10 personalized boundary conditions for font size are defined. This may be done in a variety of ways. One option is to access the patient profile data on age, eyesight, etc. and to assign the patient a pre-defined "font-size band", i.e. a number of potentially usable fonts for this patient based on his visual capabilities and reading related impairments such as dyslexia. Information on conditions such as dyslexia may also contribute and may involve modifying some fonts to include "bottom-heavy" fonts (i.e. font styles using lines that are thicker toward the bottom than at the top.

Another option is to use a game-style test to determine the "font-size band" and patient-specific optimal fonts for retention and motivation. For instance, the patient is presented with different characters and information in various sizes and fonts, and tested on what they have seen, retained and perceived.

Still another option is to use a gaze or scrolling analysis during reading to assess the patient's reading speed, which gives a useful measure of reading difficulty (for a particular font setting for a particular user). Gaze analysis will provide a more accurate reading speed than scrolling analysis. It may be achieved by use of a camera pointed to the user's eyes. Scrolling analysis is more straightforward and measures how quickly the user scrolls through a text.

In a second step S12 the patient's care plan is mined for important details that should or need to be communicated, which will include both information and activities/actions, e.g. details that should be remembered by the patient (such as low-salt recipes) or reminders for tasks (such as physical exercise). Alternatively, other reminder system may be used, in which case information to be presented may be fed directly to the present system.

This mining of the care plan can also be done based on the different activities in the care plan and which compliance hurdles (e.g. a hurdle of forgetting or a hurdle of too high perceived effort) can be expected from the patient's side. For example, for physical activity the hurdle may be based mainly on that the perceived effort is too high which would mean that the information related to physical activity should be in easy-to-read font size. For low-salt diet the hurdle may be more in the forgetting how to or which recipes to cook that contain little salt rather than that effort is perceived as too high etc.

In a third step S14 the best font for image presentation is determined depending on the information to be visualized, which will be explained in more detail below.

In a fourth step S16 the font selection is modified based on the anticipated motivation and ability of the patient to read and process the information, which may be estimated using motion and location sensors in the patient's device. For example, the following levels and rules for modifying a font may be used:
Patient at home—default level;
Patient not at home—(default −1), i.e. shift to easier font;
Patient stationary—(default +1), i.e. shift to harder font;
Patient walking—(default −1) or possibly delay;
Patient moving quickly, i.e. in car/train—(default +1).

If this assignment and modification of fonts is used in conjunction with another reminder system, the display of information may be timed to coincide with a convenient time for the patient, so that only patient activity needs be considered.

In a fifth step S18 the compliance over time is monitored to learn which fonts produce the best results in different situations or—optionally—in real-time to actively modify the font if it is detected that the task is perceived as too hard.

In a sixth step S20 the presentation of information to patients is varied based on the content and context of the information/message. For instance, for instructions for presentation of tasks an easy-to-read font (e.g. small font size) is used and for presentation of important information a harder-to-read font is used (e.g., bigger font size). For this step, an arbitration between the best font for information retention and the motivation of the patient to read information may be made, whereby the time of day, means of display, etc. may be considered. For instance, non-urgent information in hard-to-read font may be presented at a time when the patient is relaxed and able/willing to read it.

Figures 3, 6:
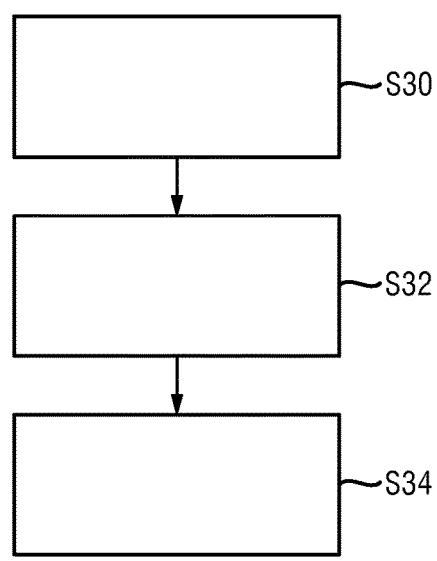
FIG. 3 shows a diagram illustrating a list of potentially usable fonts for a particular person.
FIG. 6 shows a flow chart of an embodiment of a feedback process according to the present invention.

In an embodiment to a selection of a plurality of (e.g. ten) fonts a number on a scale from easy-to-read (1) to hard-to-read (10) is assigned. An example of such an assignment is schematically shown in FIG. 3.

Figure 4:
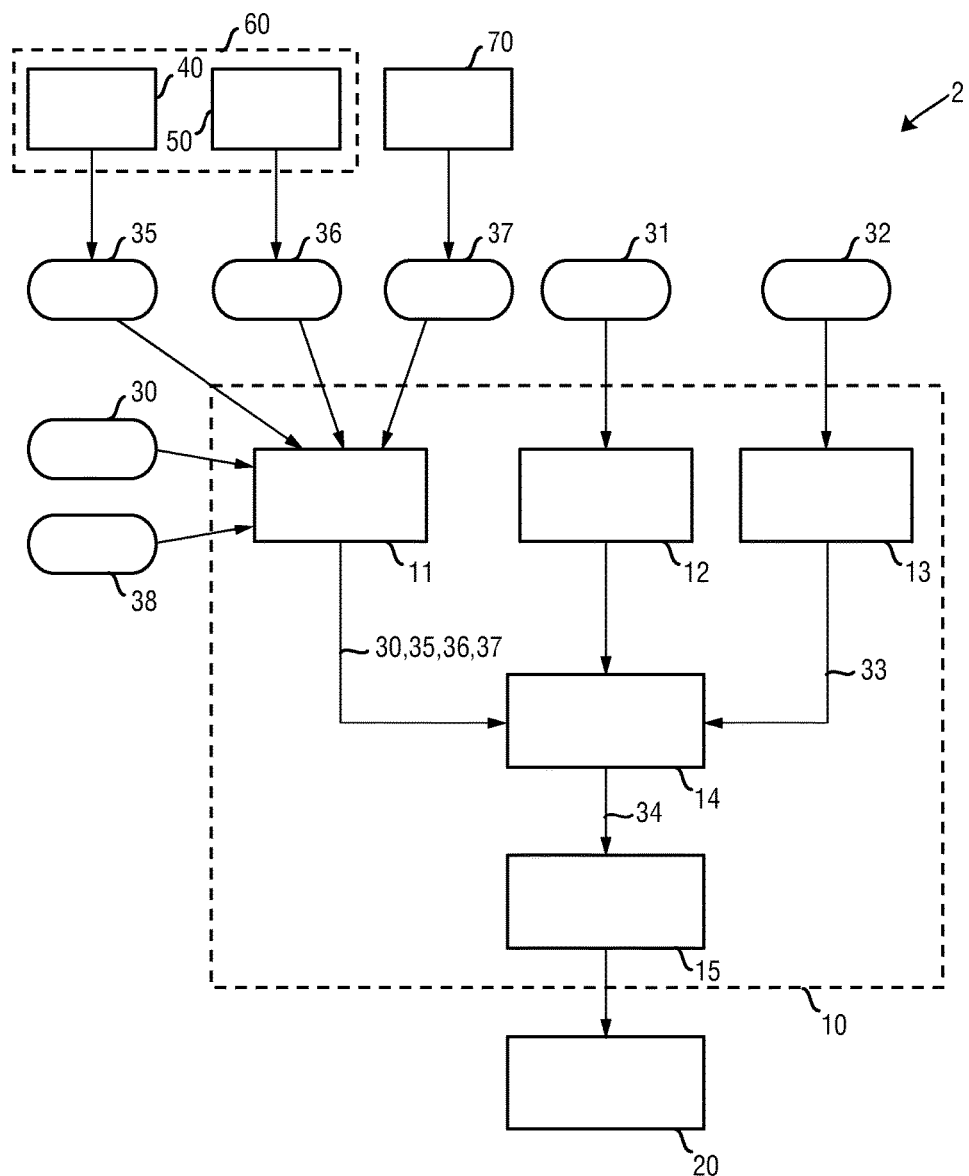
FIG. 4 shows a schematic diagram of another embodiment of a system according to the present invention.

In another embodiment of the system 2, as shown in FIG. 4, the control device 10 takes as inputs (i) the message (information) 30 to be presented, which may relate to an element of a patient's care plan, and (ii) compliance (or non-compliance) data 35 (received at the input interface 11), e.g. from a non-compliance detector 40, which may include inputs from, for example, automated pill dispensers or sensors in smart clothing.

The non-compliance detector 40 can, in the case of non-compliance, generate a non-compliance tag and recommend presenting the information again (e.g. send the message back as a new, tagged input to the system 2). In the case of compliance, the presentation style, message and element of care plan to which the message relates may be stored for future use.

Hence, in this embodiment the input interface 11 is configured to receive compliance data 35 indicating the person's compliance with a task or plan while or after being presented with information using a selected presentation style, and the controller 15 is configured to adapt and/or select the presentation style for the current and/or later presentation of information based on the importance indicator 31 and on the received compliance data 35.

Figure 5:
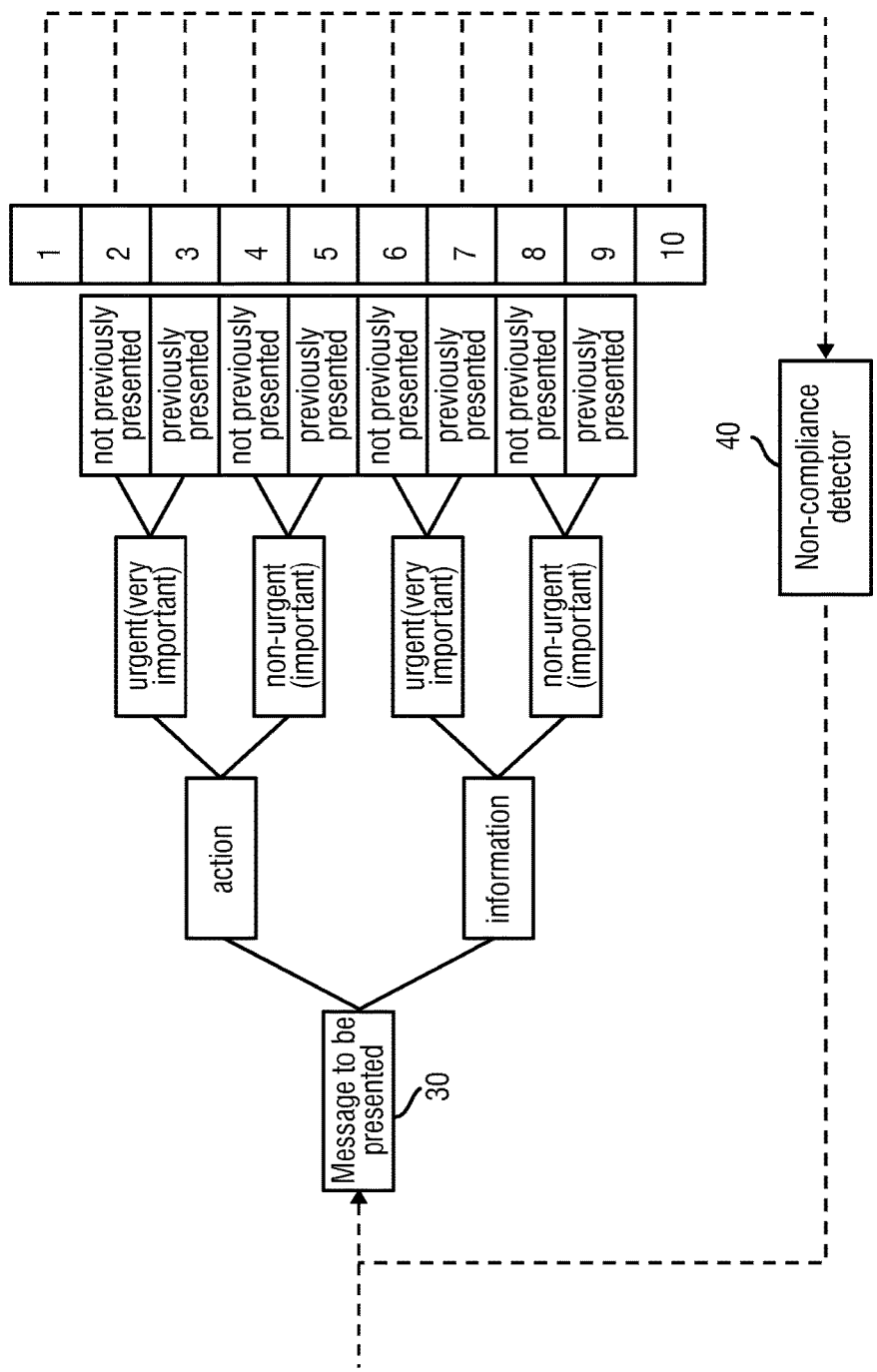
FIG. 5 shows a diagram illustration a categorization of presentation styles.

In another embodiment the information to be presented is categorized on three levels: the type of information (e.g. action, information, coaching, etc.), the importance of the information at the time of presentation (e.g. urgent/very important, non-urgent/important, average, general, etc.), and whether the information has been previously presented or not (which system may keep track of, e.g., when presenting healthcare related information using a telehealth device such as the Philips Motiva system, the system can keep track of the number of times the same information has been displayed. The combination of these categories is preferably used in this embodiment to determine the default presentation style for this information. An example of such a categorization is schematically shown in FIG. 5.

Hence, in this embodiment the importance indicator unit 11 is configured to categorize the received information 30 based on the type of the information, the importance of the information and the number of previous presentations of the information and the controller 15 is configured to select the presentation style based on the importance indicator and obtained categories of the received information. In particular, in this embodiment, the optimal presentation style number is established based on the type of information that is being presented. This presentation style number may be modified by shifting up or down based on motivation of the person. For instance, the size of a selected font is selected based on the person's personal "font size band" as e.g. defined in step S16.

Compliance data may be recorded over time along with presentation style numbers. This may be used to "learn" the presentation styles that have the best effect for a particular patient, and these could be used as "sticking presentation styles", meaning that if these presentation styles are selected during the categorizing process they will not then be shifted. Alternatively, looking at the data across different situations could also be used to set the amount of shift in step S16.

In the following further embodiments and improvements of the proposed system and method will be explained.

In an embodiment the person's sympathetic autonomic activity 36 is measured and provided as additional input to the input interface 11. This further personalizes the system 2 and makes it capable of real-time presentation style adjustments by tracking the patient's physical response to the message and implementing a feedback loop. There is a clear increase in sympathetic autonomic activity (i.e. the activity of the autonomous nervous system) when the perceived difficulty of a task increases. However, when the perceived difficulty of the task is seen as too difficult to conduct, the autonomic activity drops to its baseline level as if there is no task at all.

Hence, in this embodiment the input interface 11 is configured to receive sympathetic autonomic activity data 36 indicating the person's sympathetic autonomic activity with a task or plan while or after being presented with information using a selected presentation style and the controller 15 is configured to adapt and/or select the presentation style for the current and/or later presentation of information based on the importance indicator 31 and on the received sympathetic autonomic activity data 36

Sympathetic autonomic activity can be tracked through skin conductance or blood pressure, i.e. in general from vital signs of the person, which may be obtained by a vital signs monitor 50. The non-compliance detector 40 and the vital signs monitor 50 may be used separately, and in some embodiments only one of these units is present in the system. In other embodiments both units 40, 50 are combined into a person monitor 60.

An exemplary embodiment of the feedback process is schematically depicted in FIG. 6 and is preferably as follows. In a first step S30 an unobtrusive sensor is used to track the patient's sympathetic autonomic activity in response to reading about a certain task. In a second step S32 it is flagged when the sympathetic activity drops or does not increase compared to a baseline (normally operationalized as average of a predetermined running time window of e.g. 10 min). In a third step S34, in response to a positive flag, the presentation style is adjusted to be easier to read. This element could be built into the non-compliance detector 40, where a positive flag generates an immediate non-compliance tag and submits the message for presentation again.

In still another embodiment the system is personalized to the cognitive effort of the person as judged by parameters such as literacy. The cognitive effort required for processing has a beneficial effect on memory or an effect on perceived effort. Using presentation style (e.g. font, font style, etc.) is one way to enhance the cognitive effort, but there are further ways to trigger a more or less in-depth cognitive process, in accordance with the "levels of processing" theory, wherein levels of processing describe memory recall of stimuli as a function of the depth of mental processing (as currently e.g. described at http://en.wikipedia.org/wiki/Levels-of-processing effect). These may include i) using terms that have a personalized "intellectual challenge level" depending on someone's health literacy level, e.g. keeping a database of synonyms of terms that vary in the effort required to process them but that refer to the same thing;

ii) considering the person's psychological profile to vary the extent to which the message matches or mismatches the profile in different situations or for different messages; a mismatching tailored message would be harder to process and a matching one would be easier to process.

In this case said input interface 11 is configured to receive the person's health literacy level, psychological profile, preference for presentation style and/or education level 38, and said controller 15 is configured to select the presentation style and the wording of the information based on the importance indicator 31 and on the received person's health literacy level, psychological profile, preference for presentation style and/or education level 38.

Still further, in an embodiment the system 2 comprises a locator 70 for obtaining person-related location data and/or movement data 37 indicating the location and/or the movement state of the person, and the controller 15 is configured to select the presentation style based on the importance indicator 31 and the received person-related location data and/or movement data 37.

In the embodiment of the system 2 shown in FIG. 4 the input interface 11 and the controller 15 are shown to receive and process different kinds of information. It shall be noted that the present invention is not limited to this embodiment, but in other embodiments only a single kind of information or other combinations of kinds of information are provided to the input interface 11 and controller 15.

The importance indicator unit 12 is generally configured to receive said importance indicator 31 as input and/or to analyze the content and/or context of the received information 30 to get the importance indicator 31.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for facilitating user-task/plan-based content presentation to affect user remembrance of content, the system comprising:
   one or more sensors configured to detect, during presentation of a first content portion, sympathetic autonomic activity data indicating a user's sympathetic autonomic activity related to a task or plan of the user; and
   one or more processors configured by machine-readable instructions to:
      receive content to be presented to the user, the content comprising the first content portion;
      obtain a first importance indicator indicating an importance of the first content portion with respect to the task or plan of the user;
      obtain, based on user data related to the user, presentation style boundary conditions, the presentation style boundary conditions indicating a presentation style set from which one or more presentation styles are to be selected for presenting the content to the user, the presentation style set comprising (i) a first presentation style associated with a first difficulty level and (ii) a second presentation style associated with a second difficulty level, the second difficulty level being indicative of requiring less effort from the user to read the content than the first difficulty level;
      select, based on the first importance indicator, from the presentation style set, the first presentation style to be used over at least the second presentation style for presenting the first content portion to the user;
      cause, via a display, presentation of the content based on the selected first presentation style such that the first presentation style is used to present the first content portion on the display;
      determine, during the presentation of the first content portion, based on the sympathetic autonomic activity data, whether the user's sympathetic autonomic activity corresponds to a baseline sympathetic autonomic activity level; and
      adjust, via the display, the presentation of the first content portion based on a determination that the user's sympathetic autonomic activity corresponds to the baseline sympathetic autonomic activity level such that a presentation style that is easier to read than the first presentation style is used to present the first content portion on the display.

2. The system as claimed in claim 1, wherein the one or more processors are further configured to obtain the presentation style boundary conditions by analyzing a profile of the user including information on age, eyesight and/or ophthalmic problems of the user, by performing a test with the user and/or by analyzing gaze and/or scrolling of the user while reading text presented on the display.

3. The system as claimed in claim 1, wherein the one or more processors are further configured to receive a predetermined plan to be complied with by the user, the predetermined plan including information to be presented to the user, and to extract the information to be presented to the user from the received plan.

4. The system as claimed in claim 1, wherein the one or more processors are further configured to receive the first importance indicator as input and/or to analyze the received content and/or context of the received content to obtain the first importance indicator.

5. The system as claimed in claim 1, wherein the one or more processors are further configured to:
receive, via one or more other sensors, user-related location data and/or movement data indicating a location and/or movement state of the user; and
select the first presentation style based on the first importance indicator and the received user-related location data and/or movement data.

6. The system as claimed in claim 1, wherein the one or more processors are further configured to:
receive user-related schedule data indicating the user's schedule; and
control the display to visually present the received content at a time convenient to the user according to the user's schedule.

7. The system as claimed in claim 1, wherein the sympathetic autonomic activity data comprises skin conductance or blood pressure measurement data.

8. The system as claimed in claim 1, wherein the one or more processors are further configured to:
categorize the received content based on a type of the content, the importance of the content and a number of previous presentations of the content; and
select the first presentation style based on the first importance indicator and the categorization of the received content.

9. The system as claimed in claim 1, wherein the one or more processors are further configured to:
receive the user's health literacy level, psychological profile, preference for presentation style and/or education level; and
select the first presentation style and a wording of the content based on the first importance indicator and on the received health literacy level, psychological profile, preference for presentation style, and/or education level.

10. The system as claimed in claim 1, wherein the one or more processors are further configured to select one or more options of the first presentation style, the one or more options including font, font style, font size, font color, underline style, text effects, and/or character spacing.

11. A method for facilitating user-task/plan-based content presentation to affect user remembrance of content, the method comprising:
receiving, via one or more processors, content to be presented to a user, the content comprising a first content portion;
obtaining, via one or more processors, a first importance indicator indicating an importance of the first content portion with respect to a task or plan of the user;
obtaining, via one or more processors, based on user data related to the user, presentation style boundary conditions, the presentation style boundary conditions indicating a presentation style set from which one or more presentation styles are to be selected for presenting the content to the user, the presentation style set comprising (i) a first presentation style associated with a first difficulty level and (ii) a second presentation style associated with a second difficulty level, the second difficulty level being indicative of requiring less effort from the user to read the content than the first difficulty level;
selecting, via one or more processors, based on the first importance indicator, from the presentation style set, the first presentation style to be used over at least the second presentation style for presenting the first content portion to the user;
causing, via a display, presentation of the content based on the selected first presentation style such that the first presentation style is used to present the first content portion on the display;
detecting, via one or more sensors, during the presentation of the first content portion, sympathetic autonomic activity data indicating the user's sympathetic autonomic activity related to the task or plan of the user;
determining, during the presentation of the first content portion, based on the sympathetic autonomic activity data, whether the user's sympathetic autonomic activity corresponds to a baseline sympathetic autonomic activity level; and
adjusting, via the display, the presentation of the first content portion based on a determination that the user's sympathetic autonomic activity corresponds to the baseline sympathetic autonomic activity level such that a presentation style that is easier to read than the first presentation style is used to present the first content portion on the display.

12. The method of claim 11, wherein the content comprises the first content portion and a second content portion, the method further comprising:
obtaining, via one or more processors, a second importance indicator indicating an importance of the second content portion with respect to the task or plan of the user; and
selecting, via one or more processors, based on the second importance indicator, from the presentation style set, the second presentation style to be used over at least the first presentation style for presenting the second content portion to the user,
wherein causing the presentation of the content comprises causing, via the display, the presentation of the content based on the selected first presentation style and the selected second presentation style such that (i) the first presentation style is used to present the first content portion on the display and (ii) the second presentation style is used to present the second content portion on the display.

13. A system for facilitating user-task/plan-based content presentation to affect user remembrance of content, the system comprising:
one or more sensors configured to detect, during presentation of a first content portion, sympathetic autonomic activity data indicating a user's sympathetic autonomic activity related to a task or plan of the user; and
one or more processors configured by machine-readable instructions to:

receive content to be presented to the user, the content comprising the first content portion and a second content portion;

obtain importance indicators indicating respective importance of portions of the content with respect to the task or plan of the user, the importance indicators comprising (i) a first importance indicator indicating an importance of the first content portion with respect to the task or plan and (ii) a second importance indicator indicating an importance of the second content portion with respect to the task or plan, the first importance indicator being indicative of greater importance than the second importance indicator with respect to the task or plan;

obtain, based on user data related to the user, presentation style boundary conditions, the presentation style boundary conditions indicating a presentation style set from which one or more presentation styles are to be selected for presenting the content to the user, the presentation style set comprising (i) a first presentation style associated with a first difficulty level and (ii) a second presentation style associated with a second difficulty level, the second difficulty level being indicative of requiring less effort from the user than the first difficulty level;

select, based on the importance indicators, from the presentation style set, presentation styles to be used for presenting the content to the user, the first presentation style being selected for presenting the first content portion based on the first importance indicator, and the second presentation style being selected for presenting the second content portion to the user based on the second importance indicator;

cause, via a display, presentation of the content based on the selected presentation styles such that (i) the first presentation style is used to present the first content portion on the display and (ii) the second presentation style is used to present the second content portion on the display;

determine, during the presentation of the first content portion, based on the sympathetic autonomic activity data, whether the user's sympathetic autonomic activity corresponds to a baseline sympathetic autonomic activity level; and adjust, via the display, the presentation of the first content portion based on a determination that the user's sympathetic autonomic activity corresponds to the baseline sympathetic autonomic activity level such that a presentation style that is easier to read than the first presentation style is used to present the first content portion on the display.

* * * * *